United States Patent [19]

Arnold et al.

[11] Patent Number: 5,157,136
[45] Date of Patent: Oct. 20, 1992

[54] SINGLE-SOURCE METALLOORGANIC PRECURSORS TO PRODUCE II/VI MATERIALS

[75] Inventors: John Arnold; Phillip J. Bonasia, both of Berkeley, Calif.

[73] Assignee: Regents of the University of California, Oakland, Calif.

[21] Appl. No.: 683,275

[22] Filed: Apr. 9, 1991

[51] Int. Cl.$^5$ .......................... C07F 7/08; C07F 7/22; C07F 3/06; C07F 3/08

[52] U.S. Cl. ......................................... 556/9; 556/28; 556/81; 556/118; 556/120; 556/122; 556/123; 556/130; 546/2; 546/5; 546/6

[58] Field of Search ................ 556/9, 10, 28, 81, 118, 556/120, 122, 123, 130; 546/2, 5, 6, 4

[56] References Cited

U.S. PATENT DOCUMENTS

| | | | |
|---|---|---|---|
| 4,425,278 | 1/1984 | Wirth et al. | 556/10 X |
| 4,654,368 | 3/1987 | Sakamoto et al. | 556/9 X |
| 4,981,827 | 1/1991 | Ballard et al. | 556/81 X |
| 4,985,576 | 1/1991 | Rohrmann et al. | 556/10 X |
| 5,026,887 | 6/1991 | Kobayashi | 556/9 X |

OTHER PUBLICATIONS

G. N. Pain et al. in Polyhedron (1990) vol. 9, #7, pp. 921–929.
J. G. Brennan et al. in Chemical Materials (1990) vol. 2, pp. 403–409.
S. M. Stuczynski et al., Inorganic Chemistry (1989) vol. 28, #25, pp. 4431–4432.
A. Saunders et al. (1986) in "Ternary Multiary Compound" in Proceedings of the International Conference 7th, publ. 1987, (see Chemical Abstracts, 1988, vol. 108, #66226h).
D. M. Frigo et al., (1989) Journal of Crystal Growth, vol. 96, p. 989.
M. Bochmann et al., (1989) Angew. Chem. Int. Ed. in English, vol. 111, p. 414.
D. W. Kisker in Journal of Crystal Growth (1989), vol. 98, pp. 127–139.
B. O. Dabbousi, P. J. Bonasai & J. Arnold, J. Amer. Chem. Soc., Mar. 1991 (mailed Apr. 10, 1991).
M. B. Hursthouse et al. (1991) Organometallics, vol. 10, pp. 730–732.
Y. Takahaski et al. (1980) Journal of Crystal Growth, vol. 30, p. 491.
M. A. H. Evans and J. O. Williams (1982) Thin Solid Films, vol. 50, p. 491.

*Primary Examiner*—Arthur C. Prescott
*Attorney, Agent, or Firm*—Phillips, Moore, Lempio & Finley

[57] ABSTRACT

The present invention relates a precursor metal organic compound of the formula:

$$(R_3-Si)_3-Y-Q-M-A \qquad (I)$$

wherein M is selected from the Group IIb elements of zinc, cadmium, or mercury;

A is selected from amide, alkyl having from 1 to 10 carbon atoms, aryl, substituted aryl, or $-Q'-Y'-(Si-R'_3)_3L_2$ wherein L is selected from nothing or a Lewis base ligand, Q and Q' are each independently selected from Group VIa elements of sulfur, selenium, or tellurium; and Y and Y' are each independently selected from carbon, silicon, germanum and tin, and R and R' are each independently selected from alkyl having from 1 to 10 carbon atoms, aryl or substituted aryl.

In a preferred embodiment, A is $-Q'-Y'-(Si-R'_3)L_2$ where L is nothing or a Lewis base ligand, especially wherein Q=Q', Y=Y' and R=R'. Methods of producing these compounds are also disclosed. These precursor materials provide in a single compound the binary, tertiary or quaternary metals in a ratio to each other that is controllable by judicious choise of metal atoms and organic substituents. The metal alloys are useful in a variety of electronic applications, particularly in semiconductors.

21 Claims, 1 Drawing Sheet

SINGLE-SOURCE METALLOORGANIC PRECURSORS TO PRODUCE II/VI MATERIALS

ORIGIN OF THE INVENTION

The present invention was supported in part by a fellowship from the U.S. Department of Education.

BACKGROUND OF THE INVENTION

1. Field of the Invention

The present invention relates to the preparation of novel metal organic precursor compounds comprising at least one metal from Group IIb and at least one element from Group VIa of the Periodic Table. More specifically, the II/VI compounds are useful as single source metalloorganic tellurium or selenium, or sulfur, zinc, cadmium or mercury containing precursors useful to prepare semiconducting materials, e.g. as thin films, having precisely defined metal ratios.

*J. Am. Chem. Soc.*, (March 1991, in press)

Tris(trimethylsilyl)silyltellurol: Preparation, Characterization and Synthetic Utility of a Remarkably Stable Tellurol Bashir O. Dabbousi, Philip J. Bonasia and John Arnold*
*Department of Chemistry, University of California, Berkeley, CA 94720*

Synthetic routes to metal tellurolates, the tellurium analogues of alkoxides and thiolates, are limited.[1] Interest in these compounds heightened recently following reports that materials such as the oligomeric phenyltellurolates $[M(TePh)_2]_n$ (M = Hg, Cd) may serve as precursors to semiconducting bulk metal tellurides HgTe and CdTe.[2] We are developing tellurolate chemistry supported by large, sterically encumbered ligands in attempts to synthesize atypical metal tellurolates featuring low molecularity and hydrocarbon solubility.[3] At present, the only general route to these compounds involves a metathesis reaction between an alkali metal tellurolate and a metal halide.[4] Disadvantages include: *i*) one is limited by the choice of metal halide starting materials, *ii*) tellurolate anions are quite reducing and *iii*) the presence of strong donor molecules (either as solvent or ligated to the tellurolate salts) often interferes with product purification. In searching for more versatile routes, we considered the tellurolysis pathway outlined below:

$L_nM-X + H-TeR \rightarrow L_nM-TeR + H-X$ (R = alkyl, aryl)

Analogous reactivity is well-documented for alcohols[5], thiols[6] and selenols[7], where reactions are extremely flexible with respect to choice of R and the leaving group X (eg. X = alkyl, amide, alkoxide, etc); in addition, these reactions are best carried out in non-polar solvents. For tellurolysis, however, a major drawback has been that known tellurols are thermally unstable compounds that are difficult to isolate and purify.[8,9,10,11]

Recently we described several examples of stable sodium and potassium salts of sterically hindered aryltellurolate anions.[3] In common with earlier examples,[11] acidification of these compounds led to formation of thermally unstable tellurols and attempts at isolation and purification led only to decomposition.[12] Further investigations using sterically hindered silyl ligands have been more successful. Here we describe the synthesis and reactivity of a novel silyltellurde, its conversion to a stable silyltellurol, and the first well-defined examples of M-Te bond formation via tellurolysis.

The lithium salt $(THF)_3LiSi(SiMe_3)_3$[13] reacts cleanly with an equiv. of tellurium powder in THF at room temperature under argon or nitrogen to produce red-brown solutions of the lithium silyltellurolate 1 as shown in the Scheme. Although tellurium is known to insert into a variety of M-X bonds (X = alkyl, aryl, phosphido, etc),[14] we are unaware of any examples involving metal–silicon bonds.[15] Large yellow-green crystals of 1 were obtained from hexane in 75 % yield on scales up to ca. 20 g.[16] Evidence for the formulation of 1 is based on elemental analysis and $^1H$ NMR spectroscopy; X-ray crystallography confirmed the dimeric structure indicated in the Scheme.[17]

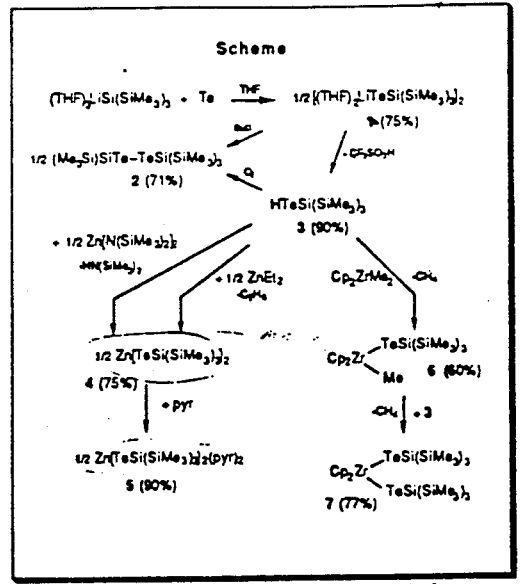

Treatment of 1 with excess oxygen in benzene-$d_6$ quickly leads to quantitative formation of emerald-green ditelluride 2 as determined by $^1H$ NMR spectroscopy; air-stable crystals were isolated from preparative scale reactions in hexane. We note that similar oxidations of aryltellurolate anions are often complex, low-yield reactions.[14,18] Cuprous chloride oxidation of 1 is an alternate high-yield route to large quantities of 1. As monitored by $^1H$ NMR spectroscopy, benzene-$d_6$ solutions of 1 were unaffected by addition of 1-4 equiv. of weak acids such as water and methanol. Addition of 1 equiv. of triflic acid to a hexane solution of 1, however, immediately produced a grey precipitate and a pale yellow-green solution. After evaporation of volatile components under reduced pressure at room temperature, the remaining residue sublimed at 40 °C ($10^{-3}$ mmHg) onto a dry-ice cooled probe to give colorless crystals of the tellurol HTeSi(SiMe$_3$)$_3$ 3 (m.p. 128-130 °C) in high yield.

A sharp singlet at unusually high field in the $^1$H NMR spectrum is assigned to the tellurol proton ($\delta$ -8.81, $J_{TeH}$ 73 Hz; $^{125}$Te, 6.99%); $v_{TeH}$ appears as a sharp, medium strength absorption at 2017 cm$^{-1}$ in the infrared. For PhTeH and MeTeH the tellurol protons are seen at $\delta$ -2.4 ($J_{TeH}$ 50 Hz),[11d,e] and $\delta$ -5.5 (no coupling constant reported).[11a-c] IR data for PhTeH were not reported but for MeTeH $v_{TeH}$ occurs at 2053 cm$^{-1}$.[11a] Compound 3 is stable under EI MS conditions showing the molecular ion at m/e = 378 ($^{130}$Te). It is exceedingly soluble in common hydrocarbon or ethereal solvents to give solutions that are stable indefinitely at room temperature under nitrogen or argon and can be heated to 130° C for at least 1 day without decomposition; however, exposing these solutions to bright sunlight results in formation of a tellurium-mirror and uncharacterized -SiMe$_3$ containing products. Solid 3 can be stored at room temperature under nitrogen for periods of up to several weeks without affecting analytical or spectroscopic properties. These results highlight the stabilizing effect of the bulky Si(SiMe$_3$)$_3$ group, particularly when one considers that trimethylsilyl tellurides, which have been known as useful synthetic reagents for some time, are extremely sensitive to protolytic cleavage by reagents such as methanol and water.[11d,e]

The synthetic value of 3 is illustrated by reactions shown in the Scheme. Tellurolysis of Zn-N and Zn-C bonds proceeds rapidly and quantitatively in hydrocarbons to give high yields of the bis-tellurolate 4 as yellow prisms from hexane or hexamethyldisiloxane. NMR tube experiments in benzene-$d_6$ showed clean formation of HN(SiMe$_3$)$_2$ in the former reaction. The complex is extremely soluble in non-polar solvents and is stable for weeks under nitrogen as a solid or in solution. The molecular structure of 4 is presently unknown, however, a tetrahedral bis-pyridine adduct 5, has now been crystallographically characterized.[12] It is important to note that conventional metathesis reactions between ZnCl$_2$ and 2 equiv. of 1 in diethyl ether or toluene gave only mixtures of compounds.[19]

Tellurolysis of Zr-Me bonds is an effective pathway to new examples of rare early transition metal tellurolates.[20] Reaction between 3 and Cp$_2$ZrMe$_2$ is sluggish below -40° C but, on warming, tellurolysis of a single Zr-Me bond proceeds rapidly around -10° C; the CH$_4$ by-product was detected in NMR tube experiments ($\delta$ 0.15). The dark orange-red methyl tellurolate complex 6 was isolated from preparative scale reactions between equimolar amounts of reactants at 20° C. It is intensely soluble in hexane (ca. 1g/mL) from which it can be crystallized at -80 °C. Tellurolysis of the remaining methyl group with a second equiv. of the tellurol is slow at room temperature but on warming to 50° C for 3h, the maroon bis-tellurolate 7 is produced in high yield.

We are now probing the reactivity of these compounds and attempting to extend the tellurolysis approach to a wider variety of main group and transition metal tellurolates.

Acknowledgement is made to the donors of the Petroleum Research Fund, administered by the American Chemical Society, for partial support of this work and the Department of Education for a fellowship (to P. J. B.).

Supplementary Material Available

Spectroscopic and analytical data for new compounds (1page).

References and Notes

1. Gysling, H. J. In: *The Chemistry of Organic Selenium and Tellurium Compounds*. S. Patai and Z. Rappoport eds. Wiley: New York, 1986, Vol 1, p 679. Gysling, H. J. *Coord. Chem. Rev.*, 1982, 42, 133.

2. Brennan, J. G.; Siegrist, T.; Carroll, P. J.; Stuczynski, S. M.; Reynders, P.; Brus, L. E.; Steigerwald, M. L. *Chem. Mater.*, 1990, 2, 403. Stuczynski, S. M.; Brennan, J. G.; Steigerwald, M. L. *Inorg. Chem.*, 1989, 28, 4431. Brennan, J. G.; Siegrist, T.; Stuczynski, S. M.; Steigerwald, M. L. *J. Am. Chem. Soc.*, 1989, 111, 9240. Steigerwald, M. L.; Sprinkle, C. R., *Organometallics*, 1988, 7, 245. Steigerwald, M. L.; Sprinkle, C. R. *J. Am. Chem. Soc.*, 1987, 109, 7200.

3. Bonasia, P. J.; Arnold, J. *J. Chem. Soc., Chem. Commun.*, 1990, 1299.

4. For examples, see: Gardner, S. A. *J. Organomet. Chem.*, 1980, 190, 289. Davies, I.; McWhinnie, W. R. *J. Inorg. Nucl. Chem. Lett.*, 1976, 12, 763, and ref 1 for reviews.

5. Bradley, D. C.; Mehrotra, R. C.; Gaur, D. P. *Metal Alkoxides*. Academic, New York. 1978. Rothwell, I. P. R.; Chisholm, M. H. In: *Comprehensive Coordination Chemistry*. Wilkinson, G., Gillard, R. D.; McCleverty, J. A. eds. Pergamon: New York. 1987, Vol 2, p 335. Caulton, K. G.; Hubert-Pfalzgraf, L. G. *Chem. Rev.*, 1990, 90, 969.

6. Dance, I. G. *Polyhedron*, 1986, 5, 1037. Blower, P. G.; Dilworth, J. R. *Coord. Chem. Rev.*, 1987, 76, 121. Vyazankin, N. S.; Bochkarev, M. N.; Charov, A. I. *J. Organomet. Chem.*, 1971, 27, 175.

7. For example: Bochmann, M.; Webb, K.; Harman, M.; Hursthouse, M. B. *Angew. Chem. Int. Ed. Engl.*, 1990, 29, 638.

8. In situ generated tellurols are useful synthetic reagents. For reactions involving addition of HTeR across C≡C bonds in acetylenes see Barros, S. M.; Dabdoub, M. J.; Dabdoub, V. M. B.; Comasseto, J. V. *Organometallics*, 1989, 8, 1661, and references therein. Reviews of organotellurium reagents in organic synthesis: Engman, L. *Phosphorus Sulfur*, 1988, 38, 105. Petragnani, N.; Comasseto, J. V. *Synthesis*, 1986, 1.

9. Irgolic, K. J. *The Organic Chemistry of Tellurium*. Gordon and Breach, New York. 1974, p 56.

10. Rauchfuss, T. B. In: *The Chemistry of Organic Selenium and Tellurium Compounds*. S. Patai ed. New York: Wiley, 1987, Vol 2, p 339.

11. Methyl tellurol reportedly explodes on contact with oxygen and is unstable above 0 °C;[11a-c] phenyl tellurol (generated in situ) decomposes at room temperature[11d,e] (a) Hamada, K.; Morishita, H. *Jpn. J. Appl. Phys.*, 1976, 15, 748. (b) Hamada, K.; Morishita, H. *Synth. React. Inorg. Met. Org. Chem.*, 1977, 7, 355. (c) Sink, C. W.; Harvey, A. B. *J. Chem. Phys.*, 1972, 57, 4434. (d) Drake, J. E.; Hemmings, R. T. *Inorg. Chem.*, 1980, 19, 1879. (e) Nagakawa, K.; Osuka, M.; Sasaki, K.; Aso, Y.; Otsubo, T.; Ogura, F. *Chem. Lett*, 1987, 1331.

12. Bonasia, P. J.; Arnold, J. manuscript in preparation.

13. Gutekunst, G.; Brook, A. G. *J. Organomet. Chem,* 1982, 225, 1.

14. Insertions into metal-carbon bonds are legion; see refs 1 and 9, p 26. Sladky has described an in situ preparation of the carbon analogue of 1, LiTeC(SiMe$_3$)$_3$, along with di- and tri-tellurides; the corresponding tellurol was not reported. Sladky, F.; Bildstein, B.; Rieker, C.; Gieren, A.; Betz, H.; Hubner, T. *J. Chem. Soc., Chem. Commun.*, 1985, 1800. Köllemann, C.; Obendorf, D.; Sladky, F. *Phosphorus and Sulfur*, 1988, 38, 69. Giselbrecht, K.; Bildstein, B.; Sladky, F. *Chem. Ber.*, 1989, 122, 1255. Giselbrecht, K.; Bildstein, B.; Sladky, F. *Chem. Ber.*, 1989, 122, 2279. Insertion of tellurium into Li-P bonds: Bildstein, B.; Sladky, F. *Phosphorus and Sulfur*, 1990, 47, 341, and refs therein.

15. Te-Si bonds are commonly made by metathesis; see: Armitage, D. A. In: *The Chemistry of Organic Silicon Compounds*. Patai, S.; Rappoport, Z. eds. Wiley, New York. 1989, and references therein. For Te insertion into a P-Si bond see: Du Mont, W. W. *Angew. Chem. Int. Ed. Engl.*, 1990, 29, 638.

16. NMR data (benzene-$d_6$, 300 MHz, 20°): 1; δ 3.75 (m, 8H), 1.43 (m, 8H), 0.45 (s, 27H). 2; δ 0.37 (s). 3; δ 0.23 (s, 27 H), -8.82 (s, 1 H). UV-VIS (hexane): 2; $\lambda_{max}$ 652 nm. Correct elemental analyses were obtained; full characterization data are provided as Supplementary Material. All (except 2) are air-sensitive and must be handled under nitrogen.

17. The structure of 2 is analogous to that for the thiolate [(THF)$_2$LiSC(SiMe$_3$)$_3$]$_2$ (Sigel, G. A.; Power, P. P. *Inorg. Chem.*, 1987, 26, 2819). A full discussion will be presented shortly.[12]

18. Engman, L.; Persson, J. *J. Organomet. Chem.*, 1990, 388, 71.

19. These mixtures were invariably contaminated with THF from 1. By contrast, cadmium and mercury analogues were readily prepared by conventional metathesis reactions giving pure M[TeSi(SiMe$_3$)$_3$]$_2$ in high yields.[12] This presumably reflects the decreased Lewis acidity of the heavier group 12 elements.

20. For examples see: Rettenmeier, A.; Weidenhammer, K.; Ziegler, M. L. *Z. Anorg. Allg. Chem.*, 1981, 473, 91. Klapötke, T. *Phosphorus, Sulfur*, 1981, 41, 105. Kopf, H.; Klapötke, T. *J. Chem. Soc., Chem. Commun.*, 1986, 1192. Sato, M.; Yoshida, T. *J. Organomet. Chem*, 1974, 67, 395. Sato, M.; Yoshida, T. *J. Organomet. Chem.*, 1975, 87, 217.

2. Description of Related Art

Semiconducting thin-film alloys can be comprised of various combinations of elements from Group IIb (II) and VIa (VI) of the standard Periodic Table. These alloys are increasingly important due to their useful electronic, optoelectronic, magnetooptic and piezoelectronic properties. These physical, chemical and electrical properties make the II/VI alloys of interest for a range of applications including, but not limited to, photovoltaic cells, infrared windows, light emitting diodes, blue-green lasers, and the like.

In the conventional processing, the growth of II/VI thin films usually involves the use of two or more different volatile, toxic metal alkyl precursor compounds, i.e., one metalloorganic compound for each metallic element to be deposited. Because each metalloorganic precursor has different reactivities, undesirable pre-reactions often occur prior to mixing and side reactions during processing usually occur which seriously limit the quality and the usefulness of the thin films of metal alloy which are produced.

These undesirable reactions can lead to difficulties in controlling the Group II/Group VI metal ratio in the resultant films, because one of the metal alkyl precursors is depleted before deposition of the desired metal alloy film on the substrate can occur. The toxicity of currently used II/VI precursor metallo-organic compounds also leads to considerable safety and environmental difficulties in storage, processing and eventual disposal. The use of two or more metalloorganic compounds requires the extra capital expense of a second (or third) precusor compound line to the reactor in which the metal alloy is produced.

At the present time, the only general synthesis route to prepare atypical metal tellurolates (or similar selenium, germanium or tin containing compounds) having a low molecular weight and solubility in organic solvents involves a metathesis reaction between an alkali metal tellurolate and a metal halide. See P. J. Bonasia et al., *Journal of the Chemical Society, Chem. Comm.*, 1990, p. 1299. S. A. Gardner, *Journal of Organometallic Chemistry*, 1980, Vol. 190, p. 280, and I. Davies et al., *Inorganic Nuclear Chemistry Letters*, 1976, Vol. 12, p. 763.

The tellurolysis pathway outlined below has not been previously reported:

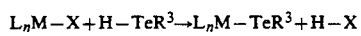

$$L_nM-X+H-TeR^3 \rightarrow L_nM-TeR^3 + H-X$$

L is a ligand

R$^3$ = alkyl, aryl

X = alkyl, amide, alkoxide, etc.

n is 0-5, (L, R$^3$, X, n defined here for this paragraph only.)

Analogous reactivity is documented for alcohols, thiols and selenols, where reactions are extremely flexible and with respect to the choice of R and the leaving group X. In addition, these reactions are best carried out in non-polar solvents. The use of silicon, germanium, or tin-containing precursors with sulfur, selenium or tellurium is not reported. Further, for tellurolysis, a major drawback has been that known tellurols are thermally unstable that are difficult to isolate and purify.

Some general reports of the production of II/VI materials using one, two or more separate metalloorganic compounds include, for example:

M. B. Hursthouse et al. (1991) *Organometallics*, Vol. 10, pp. 730–732, describes compounds of mixed alkyl dialkylthiocarbamates of zinc and cadmium. These precursors are then used for deposition of semiconductors by metallo-organic chemical vapor deposition (MOCVD).

Y. Takahaski et al. (1980) *Journal of Crystal Growth*, Vol. 50, p. 491, describes the preparation of precursors of cadmium or zinc dimethylthiophosphinates for the production of cadmium sulfide or zinc sulfide.

J. O. Williams et al. (1982) *Thin Solid Films.* Vol. 87, L1, describes the growth of highly ordered sulfide films using metal dimethylthiophosphinates.

A. Saunders et al. (1986) in "Ternary Multiary Compound" in *Proceedings of the International Conference 7th*, published 1987, (see Chemical Abstracts, 1988, Vol. 108, #66226h) describes the growth of sulfide films from zinc and cadmium thiocarbamates.

D. M. Frigo et al., (1989) *Journal of Crystal Growth*, Vol. 96, p. 989, describes sulfides of excellent crystallinity grown using bis(diethyldithiocarbamates).

M. Bochmann et al., (1989) *Angew. Chem. Int. Ed. in English*. Vol. 111, p. 414, discloses the preparation of low-coordination number complexes of cadmium and zinc with sterically hindered thiols and selenols, such as 2, 4, 6-tri-tertiary-butylbenzene-thiol.

G. N. Pain et al. in Polyhedron, (1990) Vol. 9, #7, pp. 921–929, discloses the preparation of organometallic cadmium, mercury and tellurium compounds which are used as precursors to metal alloys. Pain et al. does not teach any silicon containing precursors.

J. G. Brennan et al. in *Chemical Materials*, (1990) Vol. 2, pp. 403–409 discloses the use of separate metalloorganic II/VI precursors useful in the preparation of metallic thin films.

S. M. Stuczynski et al. in *Inorganic Chemistry* (1989), Vol. 28, #25, p. 4431 and 4432 disclose the formation of metal-chalcogen bonds by the reaction of metal alkyls with silyl chalcogenides. However, they do not teach or suggest the preparation of all metals in a single precursor compound.

D. W. Kisker in *Journal of Crystal Growth* (1989), Vol. 98, p. 127–139, discusses the II-VI family of semiconductor alloys as obtained by organometallic vapor phase epitaxy (OMVPE), particularly in applied optoelectronics.

All of the references, patents, standards, etc. referenced in this application are incorporated herein by reference.

The problems in this art remain, i.e. the reactive precursors, undesirable pre-reactions and/or side reactions. Additional disadvantages include but are not limited to:
 (i) the choice of metal halide starting materials,
 (ii) tellurolate anions are quite reducing, and
 (iii) the presence of strong donor molecules (either as solvent or ligated to the tellurolate salts) often interferes with product purification.

None of the above cited references describe a single stable silicon-containing metalloorganic compound having the metal atoms present in a particular ratio, which ratio can be varied by judicious choice of metalloorganic substitutents.

It would be extremely useful to have the metals of interest in a single stable metalloorganic precursor compound so that the ratio of the metals deposited as an alloy upon decomposition can be more precisely controlled. The present invention provides such precursor compounds and processes to produce them.

SUMMARY OF THE INVENTION

The present invention relates to a metal organic compound of the formula:

$$(R_3-Si)_3-Y-Q-M-A \qquad (I)$$

wherein M is selected from the Group IIb elements of zinc, cadmium, or mercury;

A is selected from amide, alkyl having from 1 to 10 carbon atoms, aryl, substitued aryl, or —Q'—Y'—(Si—R'$_3$)$_3$L$_2$ wherein L is selected from nothing or a Lewis base ligand, Q and Q' are each independently selected from Group VIa elements of sulfur, selenium, or tellurium; and Y and Y' are each independently selected from carbon, silicon, germanium or tin, and R and R' are each independently selected from alkyl having from 1 to 10 carbon atoms, aryl or substituted aryl.

Prefereably, the metal compound has A as —Q'—Y'—(Si—R'$_3$)$_3$ and L is nothing, especially wherein R=R', Q=Q', and Y=Y.

In one embodiment Y is silicon, especially wherein M is cadmium, and Q is selected from selenium or tellurium.

In a preferred embodiment, the metal compound has Q as tellurium, more prefereably, wherein R is alkyl, especially methyl.

In another embodiment, the metal compound has L as the Lewis base ligand which is independently selected from pyridine, substituted pyridine, pyrrole, substituted pyrrole, quinoline, morpholine, 2,2'-bipyridyl, organic phosphine, organic arsine, alkyl ether, aryl ether, thioether, amine, chelates of diamines, diphosphines, diarsines, diethers or mixtures thereof.

In another embodiment, the present invention also concerns a process for the production of a metal organic compound of the formula:

$$(R_3-Si)_3-Y-Q-M-A \qquad (I)$$

wherein M is selected from the Group II b elements of zinc, cadmium, or mercury;

A is selected from amide, alkyl having from 1-10 carbon atoms, aryl or substituted aryl, or —Q'—Y'—(Si—R'$_3$)$_3$L$_2$ wherein L is nothing or a Lewis base ligand, Q and Q' are each independently selected from Group VIa elements of sulfur, selenium, or tellurium; and Y and Y' are each independently selected from carbon, silicon, germanium or tin, and R and R' are each independently selected from alkyl having from 1 to 10 carbon atoms, aryl or substituted aryl, which process comprises:
 (A) contacting L'$_3$—Z—Y—(SiR$_3$)$_3$ wherein L' is independently selected from ligand L groups;
 Z is independently selected from lithium, sodium, potassium, calcium, barium or strontium; and Y and R are defined hereinabove, with a metal powder Q wherein Q is defined hereinabove, in a hydrocarbon solvent under an inert anhydrous atmosphere for between about 0.0i and 2 hr at between about −20° and +3° C., followed by removal of the hydrocarbon solvent;

(B) contacting the product of step (A) with a strong acid to produce and separate

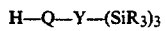

H—Q—Y—(SiR$_3$)$_3$

Q, Y and R are defined hereinabove;

(C) contacting the product of step (B) with either:
  (1) M—(NSiR$_3$)$_2$ in a 2:1 equivalent ratio in a hydrocarbon solvent at between −20° and +30° C. and for between about 0.01 and 2 hr, or
  (2) MR$_2$ in a 2:1 equivalent ratio in a hydrocarbon solvent at between about −20° and +30° C. and for between about 0.01 and 2 hr, or
  (3) M(R$^1$)$_2$ wherein R$^1$ is independently selected from amide or R as defined hereinabove in a 1:1 equivalent ratio in a hydrocarbon solvent at between about −20° and +30° C. and for between about 0.01 and 2 hr; or
  (4) M(R$^1$)$_2$ or M(NSiR$_3$)$_2$ where R' is independently selected from amide or R as defined hereinabove in a 1:1 ratio in a hydrocarbon solvent at between about −20 and +30° C. and for between about 0.01 and 2 hr followed by contacting this product with L$_3$—Z'—Y'—(SiR'$_3$)$_3$ wherein Z' is independently selected from Z, and L, Y' and R' defined hereinabove;

(D) recovering the metalloorganic compound of structure (I), where L is nothing; and (E) optionally contacting the product of step (D) with ligand L to produce the organometallic compound where L is a Lewis base.

In another aspect, the present invention relates to a process for the production of a binary, ternary or quaternary metal alloy, which process comprises:

(a) subjecting the metalloorganic compound (I) described above to a temperature of between about 150° and 500° C. in an anhydrous vacuum between about ambient pressure to 10$^{-6}$ Torr (e.g. 10$^{-2}$ tp 10$^{-6}$ Torr), especially the metal alloy producing process wherein A is —Q'—Y'—(SiR'$_3$)$_3$ and R═R', Q═Q', and Y═Y'.

DETAILED DESCRIPTION OF THE INVENTION AND PREFERRED EMBODIMENTS

Definitions

Figure 1:
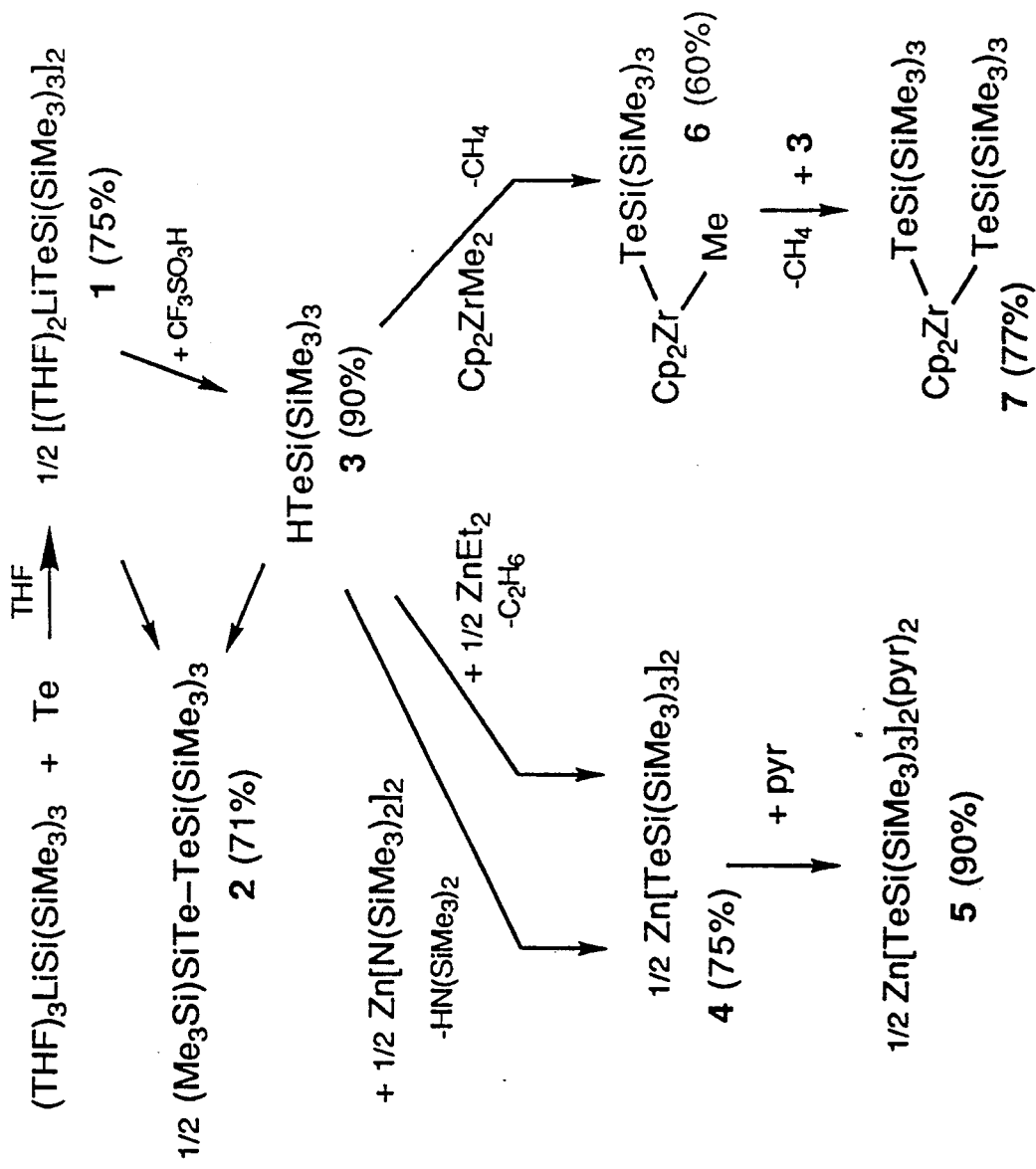
FIG. 1 is a reaction sequence which summarizes some embodiments of the present invention.

As used herein:

"Alkyl" refers to all alkyl groups usually having 1 to 20 carbon atoms. All methyl to cetyl straight chain, branched, and 4, 5 or 6 member hydrocarbon rings are also included. Methyl and ethyl are preferred.

"Aryl" refers to phenyl, naphthylene, anthracene, phenanthrene and the like. Aryl also includes groups such as -C-(phenyl)$_3$, -C(4-methylphenyl)$_3$, -C(4-methoxyphenyl)$_3$, and the like. Aryl also includes heterocyclic aryl groups such as pyridine, pyrrole, quinoline, furan, and the like. Hydrocarbons such as phenyl is preferred.

"Strong acid" refers to both mineral and organic acids. HCl, sulfuric acid, etc. are exemplary of the mineral acids. Triflic, p-toluene sulfonic, methane sulfonic acid, etc. are exemplary of strong organic acids. Triflic acid is preferred.

"Halogen" refers to fluoro, chloro or bromo.

"Substituted aryl" refers to alkyl (C1-20) or halogen substituted for one or more protons on the aryl ring. Generally 1, 2 or 3 proton substitutions are preferred. Substituted aryl also includes substituted heterocyclic aryl groups.

General Synthesis—All manipulations and transfers are carried out by using vacuum lines and standard techniques under inert atmosphere (e.g. nitrogen or argon) to exclude contact by water, oxygen or carbon dioxide.

A typical experiment is described to produce a symmetrical (with reference to the M atom) metalloorganic compound. First, L$_3$Z-Y-(SiR$_3$)$_3$ and metallic Q in a 1:1 or 2:1 molar ratio are combined, stirred, heated in an anhydrous hydrocarbon solvent, such as hexane, pentane, toluene or the like under a stream of nitrogen between about −20° to +30° C. for between about 0.01 and 2 hr, preferably between 0.5 and 1 hr. The corresponding L$_2$Z—Q—Y—(SiR$_3$)$_3$ is produced in good yield. When L$_2$Z—Q—Y—(SiR$_3$)$_3$ is treated with strong acid, e.g. triflic acid, at between about −20° and +30° C. for between about 0.01 and 2.0 hr., the corresponding H—Q—Y—(SiR$_3$)$_3$ is obtained in good yield.

Z (or Z') is independently selected from alkali metals and alkaline earth metals. Lithium, sodium, potassium and calcium are preferred. Lithium is most preferred.

Y is independently selected from sulfur, silicon, selenium or tellurium. Tellurium and selenium are preferred, especially tellurium.

L defines a ligand which is associated with the metalloorganic compound. L is independently selected from pyridine, substituted pyridine, pyrrole, substituted pyrrole, quinoline, morpholine, organic phosphine, organic arsine, alkyl ether, aryl ether, thioether, amine, or mixtures thereof, L$_2$ is also selected from 2,2'-bipyridyl, chelates of diamines, diphosphines, diarsines, diethers or mixtures thereof.

The compound M[—Q—Y—(SiR$_3$)$_3$]$_2$ can be prepared by either of two routes, as follows:

(1) H—Q—Y—(SiR$_3$)$_3$ is contacted with M—(NSiR$_3$)$_2$ in a 2:1 equivalent ratio in hydrocarbon solvent at between about −20° and +30° C. for between about 0.01 and 2.0 hr. HN(SiR$_3$)$_2$ (a liquid) is formed and separated from the reaction product by crystallization from hydrocarbon solvents.

Alternative (2), MR$_2$ (1 eq.) is contacted with H—Q—Y—(SiR$_3$)$_3$ (2 eq.) in a hydrocarbon solvent at between −20° and 30° C. (preferably ambient temperature) for between about 0.0 and 2 hr (preferably 0.05 and 0.5 hr). The corresponding (R$_3$—Si)$_3$—Y—Q—M—Q—Y—(SiR$_3$)$_3$ is isolated.

The use of a reaction ratio of 1:1 is also useful in this invention.

Alternative (3), M(R$^1$)$_2$ (1 eq) wherein R$^1$ is independently selected from amide or R as defined above, is Combined with H—Q—Y(SiR$_3$)$_3$ (1 eq) in a hydrocarbon solvent at between about −20° and 30° C. (preferably ambient temperature) for between about 0.01 and 2 hr (preferably 0.05 and 0.5 hr). The corresponding (R$_3$—Si)$_3$—Y—Q—M—R$^1$ is recovered by recystallization from hydrocarbon solvents. This compound can be decomposed to produce the metal alloy.

Alternative (4), $(R_3—Si)_3—Y—Q—M—R^1$ (i eq) is contacted with $H—Q'—Y'—(SiR'_3)_3$ (1 eq) in a hydrocarbon solvent at between about $-20°$ and $30°$ C. for between about 0.01 and 2 hr. The corresponding $(R_3—Si)_3—Y—Q—M—Y'—Q'(SiR'_3)_3$ is obtained by recystallization from hydrocarbon solvent as a solid. The two groups attached to the metal M can be the same or different as is described hereinabove. This compound is then decomposed to produce the desired metal alloy.

To obtain a binary alloy, M and Q are as defined hereinabove for alternative 1, 2 or 3.

To obtain a ternary alloy, M and Q are as defined hereinabove and Q' is present and is different from Q in Alternative 4 above.

To obtain ternary or quaternary (or higher) alloys, it is also possible to physically combine the compounds produced in Alternatives 1, 2, 3 or 4 above (as powders) to ultimately obtain the desired metal alloy ratios.

It is also possible to obtain ternary or quaternary (or higher) alloy be dissolving different compounds of Alternatives 1, 2, 3 or 4 above in a hot hydrocarbon solvent and recovering the mixed solid compounds upon cooling.

The metalloorganic compounds of the present invention are monomeric, dimeric or possibly trimeric. For this reason, they have the needed volatility to be able to be transferred within reaction lines and vessels under conventional inert atmospheric conditions. These properties are in distinction of those metalloorganic compounds of the art, which have a higher (usually much higher) degree of polymerization and organometallic compounds are essentially non-volatile. The connecting reaction lines and vessels for inert transfer is not suitable for very cumbersome.

Specific Synthesis—Referring now to FIG. 1 and the Examples, is described the synthesis and reactivity of novel silyltellurolates, conversion to a stable silyltellurol, and the first well-defined examples of M-Te bond formation via tellurolysis.

The lithium salt $(THF)_3LiSi(SiMe_3)_3$ reacts cleanly with an equivalent of tellurium powder in THF at room temperature under argon or nitrogen to produce redbrown solutions of lithium silyltellurolate 1 as shown in FIG. 1. Although tellurium is known to insert into a variety of M-X bonds (X alkyl, aryl, phosphide, etc.), there are no reported examples involving metal-silicon bonds. Large yellow-green crystals of compound 1 were obtained from hexane in 75% yield on scales up to about 20 g. Evidence for the formulation of compound 1 is based on elemental analysis and $^1H$ NMR spectroscopy; X-ray crystallography confirmed the dimeric structure indicated in FIG. 1.

Treatment of compound 1 with excess oxygen in benzene-$d_6$ quickly leads to quantitative formation of emerald-green ditelluride 2 as determined by $^1H$ NMR spectroscopy. Air-stable crystals were isolated from preparative scale reactions in hexane. Similar oxidations of aryltellurolate anions are often complex, low-yield reactions. Cuprous chloride oxidation of compound 1 is an alternate high-yield route to large quantities of compound 2. As monitored by $^1H$ NMR spectroscopy, benzene-$d^6$ solutions of compound 1 were unaffected by addition of 1-4 equivalent of weak acids such as water and methanol. Addition of 1 equivalent of triflic acid to a hexane solution of compound 1, however, immediately produced a grey precipitate and a pale yellow-green solution. After evaporation of volatile components under reduced pressure at room temperature, the remaining residue sublimed at $40°$ C. ($10^{-3}$ mmHg) onto a dry-ice cooled probe to give colorless crystals of tellurol, $HTeSi(SiMe_3)_3$, compound 3, (m.p. $128°-130°$ C.) in high yield.

A sharp singlet at unusually high field in the $^1H$ NMR spectrum is assigned to the tellurol proton ($\delta$-8.8, $J_{TeH}$ 73Hz; $^{125}Te$, 6.99%); $V_{TeH}$ appears as a sharp medium strength absorption at 2017 cm$^{-1}$ in the infrared. For PhTeH and MeTeH the tellurol protons are at $\delta$-2.4 ($J_{TeH}$ 50 Hz), and $\delta$-5.5 (no coupling constant reported). IR data for PhTeH were not reported, but for MeTeH $V_{TeH}$ occurs at 2053 cm$^{-1}$.

Compound 3 is stable under EI MS conditions showing the molecular ion at m/e=378 ($^{130}Te$). It is exceedingly soluble in common hydrocarbon or ethereal solvents to give solutions that are stable indefinitely at room temperature under nitrogen or argon and can be heated to $130°$ C. for at least 1 day without decomposition; however, exposing these solutions to bright sunlight results in formation of a tellurium mirror and uncharacterized -SiMe$_3$ containing products. Solid compound 3 is stored at room temperature under nitrogen for periods of up to several weeks without affecting analytical or spectroscopic properties. These results highlight the stabilizing effect of the bulky $Si(SiMe_3)_3$ group, particularly when one considers that trimethylsilyl tellurides, which have been known as useful synthetic reagents for some time, are extremely sensitive to photolytic cleavage by reagents such as methanol and water.

The synthetic value of compound 3 is illustrated by reactions shown in FIG. 1. Tellurolysis of Zn-N and Zn-C bonds proceeds rapidly and quantitatively in hydrocarbons to give high yields of the bis-tellurolate 4 as yellow prisms from hexane or hexa-methyldisiloxane. NMR tube experiments in benzene-$d_6$ showed clean formation of $HN(SiMe_3)_2$ in the former reaction. The complex is extremely soluble in non-polar solvents and is stable for weeks under nitrogen as a solid or in solution. A tetrahedral bis-pyridine adduct 5, is crystallographically characterized. It is important to note that conventional metathesis reactions between $ZnCl_2$ and 2 equivalents of compound 1 in diethyl ether or toluene gave only mixtures of compounds.

Tellurolysis of M'-Me, e.g. Zr-Me, bonds is an effective pathway to new examples of rare early transition metal tellurolates. M' is selected from the transition metals of Groups IB, IIIB, IVB, VB, VIB, VIIB or VIII. M' as Zn, Cr, Mo W, V, Nb or Ta are preferred. Reaction between compound 3 and $Cp_2ZrMe_2$ (wherein Cp is cyclopentadienyl) is sluggish below $-40°$ C. but, on warming, tellurolysis of a single Zr-Me bond proceeds rapidly around $-10°$ C.; the CH$_4$ by-product was detected in NMR tube experiments ($\delta$0.15). The dark orange-red methyl tellurolate complex 6 was isolated from preparative scale reactions between equimolar amounts of reactants at $20°$ C. It is highly soluble in hexane (ca. 1 g/mL) from which it can be crystallized at $-80°$ C. Tellurolysis of the remaining methyl group with a second equivalent of the tellurol is slow at room temperature, but on warming to $50°$ C. for 3 hr, the maroon bis-tellurolate 7 is produced in high yield.

Experimental Method Used for Growth of II/VI Films

Any of the precursor materials are deposited onto substrates such as quartz or GaAs in the following manner. A quartz tube containing the precursor compound and a slide o wafer of the substrate material is placed inside a resistively heated tube furnace having a temperature gradient ranging form 100°-600° C. along the length of the apparatus. The compound is placed at the cooler end of the tube while a stream of nitrogen or ammonia gas is passed through over the compound and toward the substrate. On impinging the hot substrate, the precursor compound decomposes, depositing a thin-film of II/VI alloy. The volatile decomposition products are removed in the gas stream.

Alternatively, the above process can be carried out under high vacuum ($10^{-4}$ to $10^{-6}$ torr) using the vapor pressure of the gaseous compound to transport the material to the substrate. In this case, the decomposition products condense in a part of the tube held at a much lower temperature (20°-40° C.).

Pyrolysis of Metalloorganic Compounds

The pyrolysis of the compounds by conventional means in the art is contemplated. For example, pyrolysis of $\{Zn[TeSi(SiMe_3)_3]_2\}_2$ proceeds as in the following equation:

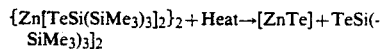

Thus, exactly 50% of the tellurium in the starting material is converted to metal telluride. The remaining 50% of tellurium is removed from the system as a volatile $TeR_2$ fragment. The starting material contains 31.28% by weight of tellurium and a film of metal telluride (ZnTe) contains 66.12% (±0.5% of tellurium is obtained.

In the related material, $Zn(Me)TeSi(SiMe_3)_3$ the following reaction occurs:

Here, 100% (±0.5%) of the tellurium in the starting material is converted to metal telluride.

Based on the work of Brennan et al. (Brennan, J. G., et al *Chem. Mater.* 1990, Vol. 2, p. 403), the compounds decompose at the substrate in following manner:

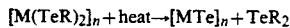

where M and R are defined above, n (here only) is the degree of polymerization=4 to 100,000 or higher.

Brennan et al. were able to demonstrate this reaction in the solid-state, but could not apply the reaction to film growth due to lack of volatility of their polymeric precursors. The diorganotelluride byproduct form is volatile and is removed by evaporation.

The following Examples are presented to further explain and describe the invention. They are not to be construed to be limiting in any way.

General. The chemical agents, reagents and solvents described herein are usually used as obtained from U.S. chemical supply houses, e.g. Aldrich Chemical Co. (catalogue), Milwaukee, Wis. These and other suitable chemical supply sources can be found in *Chemical Sources-U.S.A.*, published annually by Directories Publishing, Inc. of Columbia, S.C., all of which are incorporated herein by reference.

Standard inert atmosphere (e.g. nitrogen) techniques conventional in this art were used throughout the preparative procedures. Hexane (EM Science) and diethyl ether (Fisher) were predried over 4 Angstrom molecular sieves and distilled from sodium/benzophenone under nitrogen. Toluene (Fisher) and hexamethyldisiloxane (PCR, Inc., Gainesville, Fla.) were distilled from sodium under nitrogen. Dichloromethane and pyridine were predried over 4 Angstrom molecular sieves and distilled from calcium hydride under nitrogen. All nuclear magnetic resonance (NMR) solvents were dried in a similar manner, but were then vacuum transferred. 2,2'-Dipyridyl was purchased from Aldrich Chemical Co. (Milwaukee, Wis.) and was recrystallized from ethanol. The metal bis-trimethylsilyl amides were prepared as previously described by Burger et al., (1965) *Journal of Organometallic Chemistry*, Vol. 3, p. 113. Infrared (IR) samples Were prepared as Nujol mulls between cesium iodide (CsI) plates, and spectra were recorded on a Nicolet 510 FT-IR spectrophotometer. UV-vis spectra were recorded on a Hewlett Packard 8450 A UV-vis spectrophotometer (Palo Alto, Calif.) in 0.5cm quartz cells. 1H NMR spectra were recorded on a Bruker AM 400 MHz instrument or on a 300 MHz Nicolet spectrometer at ambient temperatures unless otherwise indicated. Chemical shifts ($\delta$) for $^1H$ NMR spectra are relative to residual protons in the deuterated solvents listed. Elemental analyses were performed by the microanalytical laboratory of the College of Chemistry, University of California, Berkeley.

EXAMPLE A

LITHIUM-TELLURIUM-SILICON INTERMEDIATE(A)

(a) $[(THF)_2LiTeSi(SiMe_3)_3]_2$(1)--Tellurium powder (1.28 g., 10.0 mmol) Was added to a tetrahydrofuran (THF) solution (200 mL) of $(THF)_3LiSi(SiMe_3)_3$ (4.70 g. (10.0 mmol) at 20° C. The mixture was stirred for 30 min, and the solvent was removed under reduced pressure. The resulting solid was dried in vacuo for 12 hours to insure removal of the THF. The solid was then extracted into hexane (200 ml), the solution was concentrated to 100 ml and cooled to −40° C. for 12 hrs. Removal of the solvent via filtration produced large, yellow needles (5.0 g., 95%) of the lithium tellurolate dimer. Compound (1) was fully characterized by NMR, IR, melting point, elemental analysis and X-ray crystallography (as a dimer).

(b) Similarly, when the reaction of Example A(a) is repeated and $(THF)_3LiSi(Si-Me_3)_3$ is replaced by a stoichiometrically equivalent amount of $(THF)_3LiSi(Si-decyl_3)_3$, the corresponding $[(THF)_2LiTeSi(Si\ decyl_3)_3]_2$ is obtained in good yield.

(c) Similarly, when the reaction of Example A(a) is repeated and $(THF)_3LiSi(SiMe_3)_3$ is replaced by a stoichiometrically equivalent amount of $(THF)_3LiSi(Si-phenyl_3)_3$, the corresponding $[(THF)_2LiTeSi(Si-phenyl_3)_3,]_2$ is obtained in good yield.

(d) Similarly, when the reaction of Example A(a) is repeated and $(THF)_3LiSi(SiMe_3)_3$, is replaced by a stoichiometrically equivalent amount of $(THF)_3LiSi(Si-4-Mephenyl_3)_3$, the corresponding $[(THF)_2LiTeSi(Si-4-Mephenyl_3)_3]_2$ is obtained in good yield.

(e) Similarly, when the reaction of Example A(a) is repeated and $(THF)_3LiSi(SiMe_3)_3$, is replaced by a stoichiometrically equivalent amount of $(THF)_3LiSn-(Si-4-Mephenyl_3)_3$, the corresponding $[(THF)_2LiTeSn-(Si-4-Mephenyl_3)_3]_2$ is obtained in good yield.

(f) Similarly, when the reaction of Example A(a) is repeated and $(THF)_3LiSi(Si-Me_3)_3$ is replaced by a stoichiometrically equivalent amount of (THF)$_3$LiSn(Si-decyl$_3$)$_3$, the corresponding [(THF)$_2$LiTeSn(Si decyl$_3$)$_3$]$_2$ is obtained in good yield.

(g) Similarly, when the reaction of Example A(a) is repeated and (THF)$_3$LiSi(SiMe$_3$)$_3$ is replaced by a stoichiometrically equivalent amount of (THF)$_3$LiSn(Si-phenyl$_3$)$_3$, the corresponding [(THF)$_2$LiTeSn(Si-phenyl$_3$)$_3$]$_2$ is obtained in good yield.

(h) Similarly, when the reaction of Example A(a) is repeated and (THF)$_3$LiSi(SiMe$_3$)$_3$, is replaced by a stoichiometrically equivalent amount of (THF)$_3$LiSn-(Si-4-Mephenyl$_3$)$_3$, the corresponding [(THF)$_2$LiTeSn-(Si-4-Mephenyl$_3$)$_3$]$_2$ is obtained in good yield.

(i) Similarly, when the reaction of Example A(a) is repeated and (THF)$_3$LiSi(SiMe$_3$)$_3$, is replaced by a stoichiometrically equivalent amount of (THF)$_3$LiGe(-SiMe$_3$)$_3$, the corresponding [(THF)$_2$LiTeGe(SiMe$_3$)$_3$]$_2$ is obtained in good yield.

(j) Similarly, when the reaction of Example A(a) is repeated and (THF)$_3$LiSi(SiMe$_3$)$_3$ is replaced by a stoichiometrically equivalent amount of (THF)$_3$LiGe(Si-decyl$_3$)$_3$, the corresponding [(THF)$_2$LiTeGe(Si-decyl$_3$)$_3$]$_2$ is obtained in good yield.

(k) Similarly, when the reaction of Example 1(a) is repeated and (THF)$_3$LiSi(SiMe$_3$)$_3$ is replaced by a stoichiometrically equivalent amount of (THF)$_3$LiGe(Si-phenyl$_3$)$_3$, the corresponding [(THF)$_2$LiTeGe(Si-phenyl$_3$)$_3$]$_2$ is obtained in good yield.

(l) Similarly, when the reaction of Example A(a) is repeated and (THF)$_3$LiSi(SiMe$_3$)$_3$, is replaced by a stoichiometrically equivalent amount of (THF)$_3$LiGe(-Si-4-Mephenyl$_3$)$_3$, the corresponding [(THF)$_3$LiTeGe(-Si-4-Mephenyl$_3$)$_3$]$_2$ is obtained in good yield.

(m) Similarly, when the reaction of Example A(a) is repeated and tellurium is replaced by a stoichiometrically equivalent amount of selenium, the corresponding [(THF)$_2$LiSeSi(SiMe$_3$)$_3$]$_2$ is obtained in good yield.

(n) Similarly, when the reaction of Example A(c) is repeated and tellurium is replaced by a stoichiometrically equivalent amount of selenium, the corresponding [(THF)$_2$LiSeSi(Si-phenyl$_3$)$_3$]$_2$ is obtained in good yield.

(o) Similarly, when the reaction of Example A(d) is repeated and tellurium, is replaced by a stoichiometrically equivalent amount of selenium, the corresponding [(THF)$_2$LiSeSi(Si-4-Mepheny13)3]2 is obtained in good yield.

EXAMPLE B

TELLUROL AND SELENOL INTERMEDIATES (a) (HTeSi(SiMe3)3(3)—Triflic acid (0.05 mL, 0.56 mmol) was added to a solution of [(THF)$_2$LiTeSi(-SiMe$_3$)$_3$]$_2$ (0.30 g. 0.28 mmol) in hexane (20 mL) at 20° C. The resulting mixture was stirred at room temperature for 2 hr. The solvent was removed by distillation under reduced pressure (10$^{-2}$ mm torr). The product was then sublimed onto a cold-finger cooled with DRY-ICE ($-78°$ C.) to give crystals (0.19 g., 90%). Compound was fully characterized by NMR, IR melting point and elemental analysis.

(b to (m)) As described in Example B(a) when the appropriate (b) to (m) compound of Example A(a) to A(m) is treated with triflic acid, the corresponding tellurol or selenol is obtained.

EXAMPLE 1

ZINC-TELLURIUM PRECURSOR (4)

(a) [Zn{TeSi(SiMe$_3$)$_3$}$_2$]$_2$ (4) - 0.625 G. (1.66 mmol) of HTeSi(SiMe$_3$)$_3$, compound 3, was dissolved in 25 ml of hexane. In a second vessel, 0.321 g (0.83 mmol) of Zn{N(SiMe$_3$)$_2$}$_2$ was similarly dissolved in 25 ml of hexane. Via cannula, tellurol solution was filtered into the solution of the zinc bis-amide at ambient temperature resulting in the immediate formation of a yellow solution from the two previously colorless solutions. The mixture was stirred for 30 min. and the solvent was removed under reduced pressure. The resulting yellow solid was further dried in vacuo for 30 min. to insure removal of the hexamethyldisilazane by-product, and then extracted with hexamethyldisiloxane (40 ml). The solution was concentrated 15 ml and cooled to about $-40°$ C. for 12 hrs. Removal of the solvent via filtration produced small, clear yellow cubes (0.504 g, 74%) of the zinc tellurolate dimer. Compound 4 begins to discolor when heated to 160° C. and from 208°-213° C. melts to a clear red-orange liquid.

$^1$H NMR (benzene-d6, 300 MHz, 20°)d 0.45(s).

IR(Nujol, CsI, cm$^{-1}$) 1277 w, 1258 s, 1244 s, 1174 w, 1034 w, 840 s, 744 m, 734 m, 689 s, 645 w, 638 w, 623 s, 462 w, 455 w, 400 w, 390 w, 303 m, 297 m. MS(E1,70 eV) m/e 816 M+), 551, 478, 73 (base peak).

Analysis: (Calculated) for C$_{18}$H$_{54}$Si$_8$Te$_2$Zn:C, 26.5; H, 6.67.

Found, C, 26.6; H, 6.87.

(b) Similarly, when the reaction of Example 1(a) is repeated and HTeSi(Si-Me$_3$)$_3$ is replaced by a stoichiometrically equivalent amount of HTeSi(Si-decyl$_3$)$_3$, the corresponding [Zn{TeSi(Si decyl$_3$)$_3$]$_2$ is obtained in good yield.

(c) Similarly, when the reaction of Example 1(a) is repeated and HTeSi(SiMe$_3$)$_3$ is replaced by a stoichiometrically equivalent amount of HTeSi(Si-phenyl$_3$)$_3$, the corresponding [Zn{TeSi(Si-phenyl$_3$)$_3$]$_2$ is obtained in good yield.

(d) Similarly, when the reaction of Example 1(a) is repeated and HTeSi(SiMe$_3$)$_3$, is replaced by a stoichiometrically equivalent amount of HTeSi(Si-4-Mephenyl$_3$)$_3$, the corresponding [Zn{TeSi(Si-4-Mephenyl$_3$)$_3$]$_2$ is obtained in good yield.

(e) Similarly, when the reaction of Example 1(a) is repeated and HTe(SiMe$_3$)$_3$, is replaced by a stoichiometrically equivalent amount of HTeSn(Si-4-Mephenyl$_3$)$_3$, the corresponding [Zn{TeSn(Si-4-Mephenyl$_3$)$_3$]$_2$ is obtained in good yield.

(f) Similarly, when the reaction of Example 1($a$) is repeated and HTeSi(SiMe$_3$)$_3$ is replaced by a stoichiometrically equivalent amount of HTeSn(Si-decyl$_3$)$_3$, the corresponding [Zn{TeSn(Si decyl$_3$)$_3$]$_2$ obtained in good yield.

(g) Similarly, when the reaction of Example 1(a) is repeated and HTeSi(SiMe$_3$)$_3$ is replaced by a stoichiometrically equivalent amount of HTeSn(Si-phenyl$_3$)$_3$, the corresponding [Zn{TeSn(Si-phenyl$_3$)$_3$]$_2$ is obtained in good yield.

(h) Similarly, when the reaction of Example 1(a) is repeated and HTeSi(SiMe$_3$)$_3$ is replaced by a stoichiometrically equivalent amount of HTeSn(Si-4-Mephenyl$_3$)$_3$, the corresponding [Zn{TeSn(Si-4-Mephenyl$_3$)$_3$]$_2$ is obtained in good yield.

(i) Similarly, when the reaction of Example 1($a$) is repeated and HTe(GeMe$_3$)$_3$, is replaced by a stoiohiometrically equivalent amount of HTeGe(SiMe$_3$)$_3$, the corresponding Zn{TeGe(SiMe$_3$)$_3$]$_2$ is obtained in good yield.

(j) Similarly, when the reaction of Example 1($a$) is repeated and HTeSi(SiMe$_3$)$_3$ is replaced by a stoichiometrically equivalent amount of HTeGe(Si-decyl$_3$)$_3$, the corresponding [Zn{TeGe(Si-decyl$_3$)$_3$}$_2$ is obtained in good yield.

(k) Similarly, when the reaction of Example 1(a) is repeated and HTeSi(SiMe$_3$)$_3$ is replaced by a stoichiometrically equivalent amount of HTeGe(Si-phenyl$_3$)$_3$, the corresponding [Zn{TeGe(Si-phenyl$_3$)$_3$}$_2$ obtained in good yield.

(l) Similarly, when the reaction of Example 1(a) is repeated and HTeSi(SiMe$_3$)$_3$, is replaced by a stoichiometrically equivalent amount of HTeGe(Si-4-Mephenyl$_3$)$_3$, the corresponding [Zn{TeGe(Si-4-Mephenyl$_3$)$_3$}$_2$ is obtained in good yield.

(m) Similarly, when the reaction of Example 1(a) is repeated and HTeSi(SiMe$_3$)$_3$ is replaced by a stoichiometrically equivalent amount of HSeSi(Si-decyl$_3$)$_3$, the corresponding [Zn{SeSi(Si decyl$_3$)$_3$}$_2$ is obtained in good yield.

(n) Similarly, when the reaction of Example 1(a) is repeated and HTeSi(SiMe$_3$)$_3$ is replaced by a stoichiometrically equivalent amount of HSeSi(Si-phenyl$_3$)$_3$, the corresponding [Zn{SeSi(Si-phenyl$_3$)$_3$}$_2$ is obtained in good yield.

(o) Similarly, when the reaction of Example 1(a) is repeated and HTeSi(SiMe$_3$)$_3$, is replaced by a stoichiometrically equivalent amount of HSeSi(Si-4-Mephenyl$_3$)$_3$, the corresponding [Zn{SeSi(Si-4-Mephenyl$_3$)$_3$}$_2$ is obtained in good yield.

EXAMPLE 2

ZINC-TELLURIUM PRECURSOR (5)

(a) Zn[TeSi(SiMe$_3$)$_3$]$_2$(pyr)$_2$ (5) - 0.331 G. (0.40 mmol) of precursor 4 was dissolved in 30 ml of hexane. Via syringe, pyridine (66, micro L, 0.80 mmol) was added to the hexane soluiton of the zinc tellurolate at ambient temperature. The clear yellow solution quickly became a lighter yellow color, and subsequently, the bis-pyridine adduct precipitated from solution as a pale yellow, microcrystalline solid. The solvent was removed under reduced pressure, and the material was extracted with dichloromethane (25 ml). The clear yellow solution was concentrated to 10 ml and cooled to about $-40°$ C. After 24 hrs., beautiful clear cubes were observed floating in the dichloromethane. Filtration of this solution produced the bis-pyridine adduct, 5, in 90% yield (0.3509 g). The crystals begin to lose pyridine at 90° C., and then slowly decompose to a dark red-orange material in a similar manner as that observed for the uncomplexed zinc tellurolate.

$^1$H NMR (CDCl$_3$, 400 MHz, 20°) d 9.00 (m, 4H), 7.79 (m,2H), 7.38 (M,4H), 0.14 (s, 54H).

IR (Nujol, CsI, cm$^{-1}$) 3069 m, 1602 s, 1573 w, 1487 s, 1448 s, 1396 m, 1357 m, 1254 m, 1241 s, 1217 m, 1153 m, 1069 s, 1037 s, 1010 s, 866 s, 750 s, 738 m, 723 m, 696 s, 689 s, 669 m, 630 s, 622 s, 423 m, 419 m, 408 m.

MS (EI, 70 eV( m/e 816 (M$^+$- 2 pyr) 624, 551, 79, 73 (base peak). Anal: Calcd for C$_{28}$H$_{64}$N$_2$Si$_8$Te$_2$Zn:C,34 5; H, 6.62; N, 2.88.

Found, C,34.4; H,6.60; N, 2.63.

(b) Similarly, the reaction of Example 2(a) is repeated and the precursor 4 is replaced by a stoichiometrically equivalent of the compound produced in Example 1(b) above, the corresponding Zn[TeSi(Si-decyl$_3$)$_3$]$_2$(pyr)$_2$ is obtained in good yield.

(c) Similarly, the reaction of Example 2(a) is repeated and the precursor 4 is replaced by a stoichiometrically equivalent amount of the compound produced in Example 1(c) above, the corresponding Zn[TeSi(Si-phenyl$_3$)$_3$]$_2$(pyr)$_2$ is obtained in good yield.

(d) Similarly, the reaction of Example 2(a) is repeated and the precursor 4 is replaced by a stoichiometrically equivalent of the compound produced in Example 1(d) above, the corresponding Zn[TeSi(Si-4-Mephenyl$_3$)$_3$]$_2$(pyr)$_2$ is obtained in good yield.

(e) Similarly, the reaction of Example 2(a) is repeated and the precursor 4 is replaced by a stoichiometrically equivalent of the compound produced in Example 1(e) above, the corresponding Zn[TeSn(SiMe$_3$)$_3$]$_2$(pyr)$_2$ is obtained in good yield.

(f) Similarly, the reaction of Example 2(a) is repeated and the precursor 4 is replaced by a stoichiometrically equivalent amount of the compound produced in Example 1(f) above, the corresponding Zn[TeSn(Si-decyl$_3$)$_3$]$_2$(pyr)$_2$ is obtained in good yield.

(g) Similarly, the reaction of Example 2(a) is repeated and the precursor 4 is replaced by a stoichiometrically equivalent amount of the compound produced in Example 1(g) above, the corresponding Zn[TeSn(Si-phenyl$_3$)$_3$]$_2$(pyr)$_2$ is obtained in good yield.

(h) Similarly, the reaction of Example 2(a) is repeated and the precursor 4 is replaced by a stoichiometrically equivalent of the compound produced in Example 1(h) above, the corresponding Zn[TeSi(SiMe$_3$)$_3$]$_2$(pyr)$_2$ is obtained in good yield.

(i) Similarly, the reaction of Example 2(a) is repeated and the precursor 4 is replaced by a stoichiometrically equivalent of the compound produced in Example 1(i) above, the corresponding Zn[TeSi(SiMe$_3$)$_3$]$_{2n}$(pyr)$_2$ is obtained in good yield.

(j) Similarly, the reaction of Example 2(a) is repeated and the precursor 4 is replaced by a stoichiometrically equivalent amount of the compound produced in Example 1(j) above, the corresponding Zn[TeSi(Si-decyl$_3$)$_3$]$_2$(pyr)$_2$ is obtained in good yield.

(k) Similarly, the reaction of Example 2(a) is repeated and the precursor 5 is replaced by a stoichiometrically equivalent amount of the compound produced in Example 1(k) above, the corresponding Zn[TeSi(Si-phenyl$_3$)$_3$]$_2$(pyr)$_2$ is obtained in good yield.

(l) Similarly, the reaction of Example 2(a) is repeated and the precursor 4 is replaced by a stoichiometrically 1 equivalent of the compound produced in Example 1(l) above, the corresponding Zn[TeSi(Si-4-Mephenyl$_3$)$_3$]$_2$(pyr)$_2$ is obtained in good yield.

EXAMPLE 3

ZINC-TELLURIUM PRECURSOR (8)

(a) Zn[TeSi(SiMe$_3$)$_3$]$_2$(bipy) (8) - 0.330 G. (0.36 mmol) of precursor 4 was dissolved in 30 ml of toluene. In a second vessel, 0.062 (0.39 mmol) of 2,2'-dipyridyl was similarly dissolved in 30 ml toluene. Via cannula, the colorless solution of the dipyridyl was filtered into the yellow solution of precursor compound 4 at ambient temperature resulting in an immediate color change to orange-red, and precipitation of the compound as a fine orange material. After 0.5 hr, the toluene was removed under reduced pressure and the light orange product was extracted with dichloromethane. The resulting dark red solution was concentrated from 75 to 45 ml in vacuo and slowly cooled to 0° C. overnight (about 20 hr). Removal of the methylene chloride left the bipyridyl adduct as very thin orange needles (0.276 g, 71%). Slower cooling of similarly concentrated solutions afforded the material as dark red diamond-shaped plates.

As a solid, the material seems to be exceedingly robust, showing few signs of decomposition below 260° C.

IR (Nujol, CsI) 1603 m), 1596(s), 1564(w), 1489(m), 1442(s), 1313(m), 1256(m), 1241(s), 1155(m), 1023(m), 1012(m), 861(s), 836(s), 722(s), 736(m), 689(s), 632(m), 621(s) Cm$^{-1}$.

MS(El, 70eV) m/e 816 (M+-bipyridyl), 551, 478, 73 (base peak).

Anal: Calcd. for $C_{28}H_{62}Si_8N_2Te_2Zn$:C,34.59; H, 6.43; N, 2.88.

Found, C,34.78; H,6.19; N, 2.75.

(b) Similarly, when the reaction of Example 3($a$) is repeated and precursor 4 is replaced by a stoichiometrically equivalent amount of HTeSi(Si decyl$_3$)$_3$, the corresponding [Zn{TeSi(Si-decyl$_3$)$_3$}$_2$($bipy$) is obtained in good yield.

(c) Similarly, when the reaction of Example 3($a$) is repeated and precursor 4 is replaced by a stoichiometrically equivalent amount of HTeSi(Si-phenyl$_3$)$_3$, the corresponding [Zn{TeSi(Si-phenyl$_3$)$_3$}$_2$(bipy) is obtained in good yield.

(d) Similarly, when the reaction of Example 3($a$) is repeated and precursor 4 is replaced by a stoichiometrically equivalent amount of HTeSi(Si-4-Mephenyl$_3$)$_3$, the corresponding [Zn{TeSi(Si-4-Mephenyl$_3$)$_3$}$_2$(bipy) is obtained in good yield.

(e) Similarly, when the reaction of Example 3($a$) is repeated and precursor 4 is replaced by a stoichiometrically equivalent amount of HTeSi(Si-4-Mephenyl$_3$)$_3$, the corresponding [Zn{TeSi(Si-4-Mephenyl$_3$)$_3$}$_2$(bipy) is obtained in good yield.

(f) Similarly, when the reaction of Example 3($a$) is repeated and precursor 4 is replaced by a stoichiometrically equivalent amount of HTeSi(Si decyl$_3$)$_3$, the corresponding [Zn{TeSi(Si-decyl$_3$)$_3$}$_2$(bipy) is obtained in good yield.

(g) Similarly, when the reaction of Example 3($a$) is repeated and precursor 4 is replaced by a stoichiometrically equivalent amount of HTeSi(Si phenyl$_3$)$_3$, the corresponding [Zn{TeSi(Si-phenyl$_3$)$_3$}$_2$(bipy) is obtained in good yield.

(h) Similarly, when the reaction of Example 3($a$) is repeated and precursor 4 is replaced by a stoichiometrically equivalent amount of HTeSi(Si-4-Mephenyl$_3$)$_3$, the corresponding [Zn{TeSi(Si-4-Mephenyl$_3$)$_3$}$_2$(bipy) is obtained in good yield.

(i) Similarly, when the reaction of Example 3($a$) is repeated and precursor 4 is replaced by a stoichiometrically equivalent amount of HTeSi(Si-4-Mephenyl$_3$)$_3$, the corresponding [Zn{TeSi(Si-4-Mephenyl$_3$)$_3$}$_2$(bipy) is obtained in good yield.

(j) Similarly, when the reaction of Example 3($a$) is repeated and precursor 4 is replaced by a stoichiometrically equivalent amount of HTeSi(Si decyl$_3$)$_3$, the corresponding [Zn{TeSi(Si-decyl$_3$)$_3$}$_2$($bipy$) is obtained in good yield.

(k) Similarly, when the reaction of Example 3($a$) is repeated and precursor 4 is replaced by a stoichiometrically equivalent amount of HTeSi(Si phenyl$_3$)$_3$, the corresponding [Zn{TeSi(Si-phenyl$_3$)$_3$}$_2$(bipy) is obtained in good yield.

(l) Similarly, when the reaction of Example 3($a$) is repeated and precursor 4 is replaced by a stoichiometrically equivalent amount of HTeSi(Si-4-Mephenyl$_3$)$_3$, the corresponding [Zn{TeSi(Si-4-Mephenyl$_3$)$_3$}$_2$(bipy) is obtained in good yield.

EXAMPLE 4

CADMIUM-TELLURIUM PRECURSOR (9)

(a) Cd[TeSi(SiMe$_3$)$_3$]$_2$ (9) - 1.00 G. (2.66 mmol) of HTeSi(SiMe$_3$)$_3$, 3, was dissolved in 25 ml of hexane. In a second vessel, 0.576 g (1.33 mmol) of Cd[N(SiMe$_3$)$_2$]$_2$ was similarly dissolved in 25 ml hexane. Via cannula, the solution of the tellurol was filtered into the cadmium bisamide solution at ambient temperature resulting in an immediate color change to yellow, from the two previously colorless solutions. The mixture was stirred for 30 min. and the hexane was removed under reduced pressure. As With the analogous zinc compound, this material was further dried in vacuuo and then extracted with hexane (40 ml). The solution was concentrated to 15 ml and cooled to about −40° C. for 12 hrs. Removal of the solvent via filtration left the cadmium compound 7 as a fine yellow powder (0.766 g, 68%) which melts in a manner similar to that of its zinc analog.

$^1$H NMR (benzene-d$_6$, 300 MHz, 20° C.) 0.43(s).

IR (Nujol, CsI) 1397(s), 1244(s), 1096(w), 1066(w), 1029(W), 838(s), 746(m), 691(s), 623(s), 457(w), 396(m) cm$^{-1}$.

MS (El, 70eV) m/e 863 (M+), 551, 478, 405, 73 (base peak).

(b) Similarly, when the reaction of Example 4($a$) is repeated and HTeSi(Si-Me$_3$)$_3$ is replaced by a stoichiometrically equivalent amount of HTeSi(Si-decyl$_3$)$_3$, the corresponding [Cd(TeSi(Si-decyl$_3$)$_3$]$_2$ is obtained in good yield.

(c) Similarly, when the reaction of Example 4($a$) is repeated and HTeSi(SiMe$_3$)$_3$ is replaced by a stoichiometrically equivalent amount of HTeSi(Si-phenyl$_3$)$_3$, the corresponding [Cd{TeSi(Si-phenyl$_3$)$_3$}$_2$ is obtained in good yield.

(d) Similarly, when the reaction of Example 4($a$) is repeated and HTeSi(SiMe$_3$)$_3$, is replaced by a stoichiometrically equivalent amount of HTeSi(Si-4-Mephenyl$_3$)$_3$, the corresponding [Cd{TeSi(Si-4-Mephenyl$_3$)$_3$}$_2$ is obtained in good yield.

EXAMPLE 5

CADMIUM-TELLURIUM PRECURSOR (10)

(a) Cd[TeSi(SiMe$_3$)$_3$]$_2$ (bipy) (10) - 0.300 G. (0.35 mmol) of precursor 9 of Example 4($a$) was dissolved in 25 ml of toluene. In a second vessel, 0.047 g (0.30 mmol) of 2,2'-dipyridyl was similarly dissolved in 25 ml toluene. Via cannula, the colorless solution of the bipyridyl was filtered into the yellow solution of precursor 7, resulting in the formation of red-pink solution. After complete addition of the dipyridyl, the solution remained a clear red color for several minutes, quickly becoming orange-yellow. Within several minutes the compound precipitated out of solution as a fine yellow material. The toluene was removed under reduced pressure and the yellow material was extracted with dichloromethane. The resulting dark orange-red solution was concentrated and cooled to −40° C. After 12 hrs, the solvent was removed via filtration leaving the bipyridyl adduct as very thin yellow needles (0.233 g, 76%). This material displays a similar robustness as the analogous zinc compound with little decomposition noticeable below 240° C.

IR (Nujol, CsI) 1597(m), 1488(m), 1439(s), 1311(m), 1257(m), 1240(s), 1100(w), 1061(w), 1015(m), 861(s), 836(s), 767(m), 688(m), 648(m), 622(m), 420(w), 403(w) cm$^{-1}$.

MS (El, 70eV) m/e 863 (M+ -bipyridyl), 551, 478 73 (base peak).

Anal. Calcd. for $C_{28}H_{62}Si_8N_2Te_2Cd$: C,33.00; H, 6.13; N, 2.75.

Found, C,32.75; H,5.88; N, 2.48.

(b) Similarly, when the reaction of Example 5(a) is repeated and the precursor 3 of Example 4(b) is replaced by a stoichiometrically equivalent amount of HTeSi(Si-decyl$_3$)$_3$, the corresponding [Cd{TeSi(Si decyl$_3$)$_3$}]$_2$ is obtained in good yield.

(c) Similarly, when the reaction of Example 5(a) is repeated and the precursor 3 of Example 4(c) is replaced by a stoichiometrically equivalent amount of HTeSi(Si-phenyl$_3$)$_3$, the corresponding [Cd(TeSi(Si phenyl$_3$)$_3$}]$_2$ is obtained in good yield.

(d) Similarly, when the reaction of Example 5(a) is o repeated and the precursor 3 of Example 4(d) is replaced by a stoichiometrically equivalent amount of HTeSi(Si-4-Mephenyl$_3$)$_3$, the corresponding [Cd{TeSi(Si-4-Mephenyl$_3$)$_3$}]$_2$ is obtained in good yield.

EXAMPLE 6

MERCURY-TELLURIUM PRECURSOR (11)

(a) Hg[TeSi(SiMe$_3$)$_3$]$_2$ (11) - 0.753 G. (2.0 mmol) of HTeSi(SiMe$_3$)$_3$, compound 3, was dissolved in 30 ml of hexane. In a second vessel, 0.500 g (1.0 mmol) of Hg[N(SiMe$_3$)$_2$]$_2$ was similarly dissolved in 30 ml hexane. Via cannula, the solution of the tellurol was filtered into the mercury bisamide solution at ambient temperature resulting in an immediate color change to yellow, from the two previously colorless solutions. Before the entire volume of the tellurol had been added, however, the color of the mixture began to darken and became slightly brown. After stirring for 30 min, no further darkening was observed, and the solvent was removed under reduced pressure. The resulting yellow-brown material was extracted with hexamethyldisiloxane leading to a yellow solution which was filtered, concentrated, and cooled to about 40° C. After 24 hrs, removal of the solvent afforded the product (0.778 g, 82%) as transparent green crystals. Compound 8 behaves very much like its zinc and cadmium analogs, as heating of the solid results in a transformation to a red-orange liquid. In the case of mercury tellurolate 8, this change is observed at 128° C.

1H NMR (benzene-d$_6$, 300 MHz, 20° C.) 0.315(s).

IR (Nujol, CsI) 1444(s), 1394(s), 1256(s), 1241(s), 1097(m), 1031(w), 834(s), 744(s), 688(s), 622(s), 459(W) cm$^{-1}$.

MS (e1,70 eV) m/e 951 (M+), 551, 478, 73 (base peak).

UV-Vis pentane, 5.3×10$^{-5}$M): lmaX 289nm ($\epsilon$=38, 491 Lmol- 1cm$^{-1}$), Imax 272nm ($\epsilon$=47 811 Lmol$^{-1}$cm$^{-1}$).

Anal. Calcd. for $C_{18}H_{54}Si_8Te_2Hg$: C,22.73; H, 5.72.

Found, C,22 54; H,5.87.

(b) Similarly, when the reaction of Example 6(a) is repeated and HTeSi(Si-Me$_3$)$_3$, 3, is replaced by a stoichiometrically equivalent amount of HTeSi(Si-decyl$_3$)$_3$, the corresponding [Hg{TeSi(Si decyl$_3$)$_3$}]$_2$ is obtained in good yield.

(c) Similarly, when the reaction of Example 6(a) is repeated and HTeSi(SiMe$_3$)$_3$, 3, is replaced by a stoichiometrically equivalent amount of HTeSi(Si-phenyl$_3$)$_3$, the corresponding [Hg(TeSi(Si phenyl$_3$)$_3$}]$_2$ is obtained in good yield.

(d) Similarly, when the reaction of Example 6(a) is repeated and HTeSi(SiMe$_3$)$_3$, 3, is replaced by a stoichiometrically equivalent amount of HTeSi(Si-4-Mephenyl$_3$)$_3$, the corresponding [Hg{TeSi(Si-4-Mephenyl$_3$)$_3$}]$_2$ is obtained in good yield.

While only a few embodiments of the invention have been shown and described herein, it will become apparent to those skilled in the art that various modifications and changes can be made in the process to produce a stable single precursor compound having two or more metal atoms useful to produce metal alloys having a defined metal atom ratio and the precursors thereof without departing from the spirit and scope of the present invention. All such modifications and changes coming within the scope of the appended claims are intended to be carried out thereby.

We claim:

1. A metal compound of the formula:

$$(R_3-Si)_3-Y-Q-M-A \qquad (I)$$

wherein M is selected from the Group IIb elements of zinc, cadmium, or mercury;

A is selected from amide, alkyl having from 1 to 20 carbon atoms, aryl, substituted aryl, or —Q'—Y'—(Si—R'$_3$)$_3$L$_2$ wherein L is selected from nothing or a Lewis base ligand, Q and Q' are each independently selected from Group VIa elements of sulfur, selenium, or tellurium; and Y and Y' are each independently selected from carbon, silicon, germanum or tin, and R and R' are each independently selected from alkyl having from 1 to 20 carbon atoms, aryl or substituted aryl.

2. The metal compound of claim 1 wherein A is —Q'—Y'—(Si—R'$_3$)$_3$ and L is nothing.

3. The metal compound of claim 2 wherein R=R', Q=Q', and Y=Y'.

4. The metal compound of claim 3 wherein Y is silicon.

5. The metal compound of claim 4 wherein Q is selected from selenium or tellurium.

6. The metal compound of claim 5 wherein Q is tellurium.

7. The metal compound of claim 6 wherein M is cadmium, and Q is selected from selenium or tellurium.

8. The metal compound of claim 6 wherein M is zinc.

9. The metal compound of claim 6 wherein M is mercury.

10. The metal compound of claim 6 wherein R is alkyl.

11. The metal compound of claim 10 wherein R is methyl.

12. The metal organic compound of claim 1 wherein L, the Lewis base ligand is present and is independently selected from pyridine, substituted pyridine, pyrrole, substituted pyrrole, quinoline, morpholine, 2,2'bipyridyl organic phosphine, organic arsine, alkyl ether, aryl ether, thioether, amine, chelates of diamines, diphosphines, diarsines, diethers or mixtures thereof.

13. The metal organic compound of claim 9 wherein L is pyridine, or 2,2'-bipyridyl.

14. The metal organic compound of claim 6 wherein L, the Lewis base ligand is present and is independently selected from pyridine, substituted pyridine, pyrrole, substituted pyrrole, quinoline, morpholine, 2,2'bipyridyl organic phosphine, organic arsine, alkyl ether, aryl ether, thioether, amine, chelates of diamines, diphosphines, diarsines, diethers or mixtures thereof.

15. The metal compound of claim 14 wherein M is cadmium.

16. The metal compound of claim 14 wherein M is zinc.

17. The metal compound of claim 14 wherein M is mercury.

18. A process for the production of a metal organic compound of the formula:

$$(R_3-Si)_3-Y-Q-M-A \qquad (I)$$

wherein M is selected from the Group II b elements of zinc, cadmium, or mercury;

A is selected from amide, alkyl having from 1 to 20 carbon atoms, aryl, substituted aryl, or $-Q'-Y'-(Si-R'_3)_3L_2$ wherein L is nothing or a Lewis base ligand, Q and Q' are each independently selected from Group VIa elements of sulfur, selenium, or tellurium; and Y and Y' are each independently selected from carbon, silicon, germanum or tin, and R and R' are each independently selected from alkyl having from 1 to 20 carbon atoms, aryl or substituted aryl, which process comprises:
(A) contacting $L'_3-Z-Y-(SiR_3)_3$ wherein L' is independently selected from ligand L,
    Z is independently selected from lithium, sodium, potassium, calcium, barium or strontium; and
    Y and R are defined hereinabove, with a metal powder Q wherein Q is defined hereinabove, in a hydrocarbon solvent under an inert anhydrous atmosphere for between about 0.0 and 2 hr at between about $-20°$ and $+30°$ C.;
(B) contacting the product of step (A) with a strong acid to produce and separate by removal of the hydrocarbon solvent $$H-Q-Y-(SiR_3)_3$$

where Q, Y and R are defined hereinabove;
(C) contacting the product of step (B) with:
    (1) $M-(NSiR_3)_2$ in a 2:1 ratio in a hydrocarbon solvent at between $-20°$ and $+30°$ C. and for between about 0.01 and 2 hr, or
    (2) $MR_2$ in a 2:1 ratio in a hydrocarbon solvent at between about $-20°$ and $+30°$ C. and for between about 0.01 and 2 hr, or
    (3) $M(R^1)_2$ or $M(NSiR_3)_2$ wherein $R^1$ is independently selected from amide or R as defined hereinabove in a 1:1 ratio in a hydrocarbon solvent at between about $-20°$ and $+30°$ C. and for between about 0.01 and 2 hr, or
    (4) $M(R^1)_2$ or $M(NSiR_3)_2$ wherein $R^1$ is independently selected from amide or R as defined hereinabove in a 1:1 ratio in a hydrocarbon solvent at between about $-20°$ and $+30°$ C. and for between about 0.01 and 2 hr, followed by treatment with one equivalent of $H-Q'-Y'-(SiR'_3)_3$, where Q', Y' and R' are defined above, in a hydrocarbon solvent at between about $-20°$ and $+30°$ C. for between about 0.01 and 2 hr;
(D) recovering the metalloorganic compound of structure (I), where L is nothing; and
(E) optionally contacting the product of step (D) with ligand L to produce the organometallic compound where L is a Lewis base.

19. The process of claim 18 wherein L is present and is a Lewis base.

20. A process for the production of a di-, tri- or tetrametal alloy, which process comprises:
(F) subjecting the metalloorganic compound step (D) or step (E) of claim 18 to a temperature of between about 150° and 500° C. in an anhydrous vacuum between about ambient pressure to $10^{-6}$ Torr.

21. The process of claim 18 wherein A is $-Q'-Y'-(SiR'_3)_3$ and R=R', Q=Q', and Y=Y', and L is nothing.

* * * * *